United States Patent [19]
Smith

[11] Patent Number: 5,344,775
[45] Date of Patent: Sep. 6, 1994

[54] SYNTHESIS OF TAXANES IN CULTURE USING PSEUDOCALLUSCELLS

[75] Inventor: Richard J. Smith, Atherton, Calif.

[73] Assignee: Escagenetics Corporation, San Carlos, Calif.

[21] Appl. No.: 794,711

[22] Filed: Nov. 15, 1991

[51] Int. Cl.$^5$ .......................... C12N 5/00; C12P 1/00
[52] U.S. Cl. ................................. 435/240.48; 435/41
[58] Field of Search .............................. 435/240.48, 41

[56] References Cited

U.S. PATENT DOCUMENTS

| | | | |
|---|---|---|---|
| 4,152,214 | 5/1979 | Delfel et al. | 195/104 |
| 4,827,079 | 5/1989 | Evans et al. | 435/240.51 |
| 4,910,138 | 3/1990 | Miura et al. | 435/119 |
| 5,015,744 | 5/1991 | Holton | 549/510 |
| 5,019,504 | 5/1991 | Christen et al. | 435/123 |

OTHER PUBLICATIONS

Collinge, M., Trends in Biotech. 4:299–301 (1986).
Delfel, N. E. and Rothfus, J. A., Phytochem. 16:1595–1598 (1977).
DiCosmo, F. and Tallevi, S. G., Trends in Biotech. 3(5):110–111 (1985).
Misawa, M., Production of Natural Substances by Plant Cell Cultures Described in Japanese Patents. pp. 24–26.
Misawa, M. et al., Proc. 5th Intl. Cong. Plant Tissue & Cell Culture (1982). pp. 279–280.
Misawa, M. et al., Planta Medrea 49:115 (1983).
Vidensek, N. et al., J. Natural Products 53(6):1609–1610 (1990).
Wani, M. C. et al., J. Amer. Chem. Soc. 93(9) (1971).
Yamada, Y. and Fujita, Y., Production of Useful Compounds in Culture (in *Handbook of Plant Cell Culture*, vol. 1, David A. Evans et al., eds.).

*Primary Examiner*—Douglas W. Robinson
*Assistant Examiner*—Deborah K. Ware
*Attorney, Agent, or Firm*—Jacques M. Dulin

[57] ABSTRACT

A method of synthesis of taxanes from pseudocallus of Taxus species, particularly *T. baccata*, and methods for pseudocallus production are described. Pseudocallus of the invention can be distinguished from callus tissue and cell suspensions by (1) its unique morphology which is characterized by an amorphous aggregation of cells lacking both differentiated tissues and clearly defined meristematic zones; by (2) very poor intercellular adhesion resulting in marked tissue friability; and by (3) relatively high initial rate of mass doubling. Production of taxanes is achieved by culturing the pseudocallus on support culture medium.

19 Claims, 3 Drawing Sheets

SYNTHESIS OF TAXANES IN CULTURE USING PSEUDOCALLUSCELLS

FIELD OF THE INVENTION

The present invention relates to plant-produced secondary compounds and more particularly to the production of taxanes and related secondary compounds from plant pseudocallus tissue.

REFERENCES

Bailey, L. H., Manual of Cultivated plants, McMillan Co, New York, N.Y. (1949).

Britten, N. L., et al., An illustrated Flora of the Northern United States and Canada (1970).

Brossi et al. (eds.) 1985. The Alkaloids, Chemistry and Pharmacology 25:6–18, 280–288.

Collinge. 1986. Tibtech 4:299–301.

Den Oudin, P., et al., Manual of Cultivated Conifers, (1965).

DiCosmo et al. Trends in Biotechnology 3:110–111.

Einsig et al. 1988. Proc Amer. Soc. Clin. Oncologists 7:249.

Evans et al. (eds.) 1983. Handbook of Plant Cell Culture, Vol. 1, pp. 717–720.

Huang et al. 1986. J. Natural Products. 49:665–669.

Misawa et al. 1982. Proc. 5th Intl. Congress of Plant Tissue & Cell Culture. pp 279–280.

Misawa, et al., 1982. Medical Plant Research, 49:115. Martinus Nijoff, The Hague, Holland (1965).

Rehdar, A., Manual of Cultivated Trees and Shrubs Hardy in North America, McMillan. N.Y. (1947).

Rohr. 1973. Caryologia 25:177–189.

Rohr. 1982. Can. J. Bot. 60:1583–1589.

Rowinsky et al. 1988. Proc. Amer. Soc. Clin. Oncologists 7:136.

Rowinsky, E. K., et al., Cancer Res. 48(14):4093 (1988).

Sargent, E. S., Manual of Trees of North America, Dover Publication, N.Y. (1965).

Vidensek. 1990. J. Natural Products. 53:1609–1610.

Wani et al. 1971.J. Amer. Chem. Soc. 93:9–11.

Witherrup, K. M., et al., J Nat Products, 53(5):1249 (1990).

Zentkeller et al, 1970. Acta Soc. Bot. Pol. 39:161–173.

BACKGROUND OF THE INVENTION

Higher plants produce a variety of secondary metabolic compounds, such as alkaloids, which are useful in the treatment of human diseases. One recently discovered alkaloid group, the taxanes, includes taxol, a diterpenoid sesquiterpene that exhibits strong antineoplastic activity and shows great promise in the treatment of leukemia, melanoma, breast cancer and ovarian cancer. (Brossi, Einsig, Rowinski, Wani).

Taxol was originally isolated from the bark and leaves of the Pacific Yew, Taxus brevifolia Nuttall, where it is present in minute quantities, generally less than 0.015% by weight of tissue extracted (Vidensk). Taxol has been isolated from other species of Taxus such as T. cuspidata, T. baccata, and T. media. The amount of taxol obtainable from different Taxus species is variable (Vidensk, Wani). This source of taxol is quite limited, due to the large number of trees which must be harvested to obtain therapeutic amounts of the compound. It has been estimated that dozens of trees may be required to obtain a therapeutic dose for a single patient. Unfortunately the best natural plant source of taxol is T. brevifolia, a slow-growing tree restricted to a narrow geographical range in old growth, mixed-conifer forest in the Pacific Northwest.

Synthetic production of taxol has proved impractical, due to the complexity of the alkaloid synthesis. Semi-synthetic methods of taxol production, in which a taxol precursor is converted to taxol synthetically has also been proposed (U.S. Pat. No. 5,015,744). The semi-synthetic method is also impractical at present, due to the difficulty in obtaining purified precursors.

It has been suggested that the limitations in taxol production might be overcome through the use of tissue culture techniques to produce secondary metabolites, including taxol. Success, however, requires first obtaining cells which are capable of sustained growth in culture, and secondly, inducing such cells to produce adequate quantities of the desired metabolite. In particular, the production of significant amounts of secondary metabolites in tissue culture has met with numerous difficulties. (Collinge, Dicosmo, Evans; see also U.S. Pat. No. 4,910,138 to Miura et al., column 1, lines 18–35)

One source of difficulty is that cultured cells often fail to synthesize the desired metabolite in culture. Although callus tissue may contain some concentration of secondary metabolites at the time of callus induction, subsequent subcultures of the callus display progressively lower concentrations of secondary metabolites. In such cases, tissue culture production of secondary metabolites can be ineffective because it requires continual harvest of explants from differentiated plant bodies. Secondary metabolite production is further limited because production is often contingent on cell differentiation or organization of the cells into organized tissues.

Production of sporophyte-derived callus tissue and extraction of taxol therefrom has been reported for T. brevifolia (U.S. Pat. No. 5,019,804 to Christen et al.). The method disclosed in the '504 patent for production of taxol from culture follows the procedure disclosed earlier by Misawa et al. (Misawa, 1982, 1983) for the production of a variety of antineoplastic drugs from plant tissue cultures, including taxol from T. brevifolia. The method involves inducing callus from explants of the selected plant source, e.g., T. brevifolia, growing the callus cells in a cell suspension, and isolating the desired secondary metabolite antineoplastic agent, e.g., taxol, from the suspension culture. In studies conducted in support of the present invention, the approach generally disclosed in the '504 has yielded levels of taxane which are in the range of a few parts per billion fresh tissue weight.

SUMMARY OF THE INVENTION

It is a general object of the invention, therefore, to provide an improved method for producing taxanes in culture, and to provide callus-derived cells effective to produce high levels of taxanes in culture.

In one aspect, the invention includes a method of producing taxanes (including taxol) in cultured cells. The method includes, first, obtaining from explants of Taxus baccata, a pseudocallus having the form of a loose, amorphous aggregation of undifferentiated cells without substantial intercellular adhesion. The pseudocallus is cultured on a support culture medium until a selected level of taxanes is produced in the cells, and this material is then isolated from the cells.

In a preferred embodiment, the medium is a semi-solid medium containing Gelrite ® as a solidifying agent, the culturing is carried out in an atmosphere which is substantially free of ethylene and has reduced concentration of $CO_2$, and the selected level of taxanes in the cells is at least about 25 μg/g fresh weight of pseudocallus is attained.

In another aspect, the invention includes a method for obtaining from explants of a selected species of Taxus, such as *T. baccata*, a pseudocallus. In practicing the method, fragments of callus tissue induced from Taxus explants are cultured under cell-suspension growth conditions, to produce a suspension of callus-derived cells. These cells are then plated on a support culture medium, and allowed to divide on the culture medium to form the pseudocallus. The rate of mass doubling of the cells on the culture medium is significantly greater than that of callus tissue obtained from the same Taxus species grown on the same support medium.

In a preferred embodiment of the invention, the pseudocallus is derived from plant explants from *T. baccata*, and the support medium is a non-agar based semi-solid medium. One exemplary pseudocallus derived from *T. baccata* is obtained from a suspension of cells identified as Escagenetics Cell Line 90T1. The cells of the pseudocallus produce taxanes, and can accumulate taxanes to a level of up to 50 μg taxanes/g fresh weight of pseudocallus.

Also forming part of the invention is pseudocallus derived from explants of a species of Taxus, and characterized by (a) a loose, amorphous aggregation of undifferentiated Taxus cells without substantial intercellular adhesion; and (b) a rate of mass doubling, when the cells are grown on fresh support culture medium, which is twice that of callus cells grown under the same conditions.

One preferred pseudocallus is derived from explant material from *T. baccata* 'resembling Hessei', as exemplified by a pseudocallus identified as Escagenetics Cell Line No. 90T1. When grown on a support medium, the cells of the pseudocallus are capable of accumulating taxanes, including taxol, to a level of up 50 μg taxanes/g fresh weight of pseudocallus or higher.

In a related aspect, the invention includes cultured cells derived from Taxus plant tissue, and containing at least 25 μg taxanes/g fresh weight of cells, and up to 50 μg taxanes/g fresh weight of cells or higher.

These and other objects and features of the invention will become more fully apparent when the following detailed description of the invention is read in conjunction with the accompanying drawings.

DETAILED DESCRIPTION OF THE INVENTION

I. Production and Culture of Pseudocallus

Figure 1A:
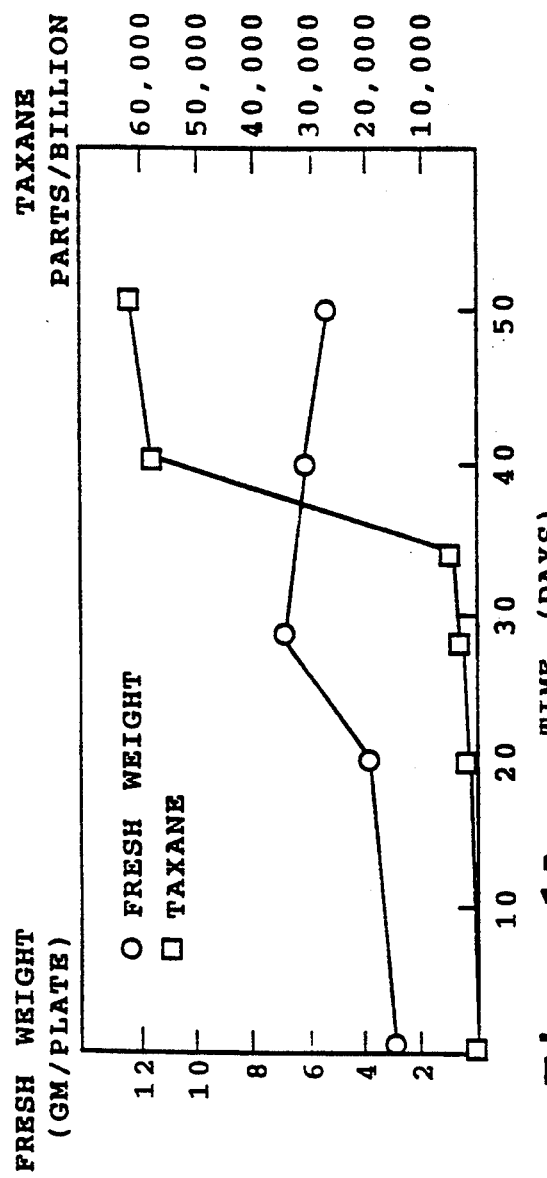
FIG. 1A shows a time course of pseudocallus growth (squares) and pseudocallus taxane production (circles) from a cell line of *T. baccata*.

The production and culture of a novel tissue culture type, herein referred to as pseudocallus, is described in this section. Part A and Examples 1-2 describe the derivation, production and culture of callus tissue from Taxus species. Part B and Example 3 describe the production of a cell suspension from fragments of Taxus callus. Part C and Example 4 describes the induction and maintenance of pseudocallus cells in culture.

A. Induction of Callus Tissue

A variety of Taxus species, including *T. baccata*, *T. brevifolia*, *T. cuspidata*, and *T. media*, may be used for the preparation of callus, and ultimately pseudocallus, although *T. baccata* is preferred. Many of these species are popular as ornamental plants and thus may be obtained from commercial sources such as nurserymen. *Taxus brevifolia* is rarely cultivated, but is native to the Pacific Northwest of the United States and is occasionally available from native plant nurseries in California, Oregon and Washington.

Propagation of Taxus species follows standard techniques well known to horticulturalists, as further detailed in Example 1. Although Taxus may be propagated from seeds, it is preferred to propagate a desired plant asexually from cuttings. This method is advantageous over seed-based propagation in that it avoids mixes associated with sexual reproduction, thereby maintaining a preferred genotype.

For purposes of species identification, the following leaf morphologies of *T. baccata* and *T. brevifolia* were used. For *T. brevifolia*, the leaves are very dark green above, and are thin, with a distinctly gray cast to the stomatal bands on the underside of the leaves. Leaf length average is about 2.18 cm. The stomates are in relatively irregular lines with each band containing about seven lines (range five to eight). The midribs above were raised for about ½ to ¾ the length of the leaves. The green margins beneath are about as wide as the midrib and there was a slight gray-green band on either side of the stomatal band. The underside of the leaves are flat to very slightly convex.

For *T. baccata*, the stomatal bands on leaves are greenish-gray, rather than distinctly gray. Stomatal lines are quite regular, not irregular, and are about 10 (8-12) in number. The green margins are slightly revolute (curved downwards) so that the central portion of the lower surface appears slightly depressed. There are two relatively wide slightly blue-gray bands on either side of the stomatal band. Leaf length average is about 2.8 cm. The midrib on the upper side of the leaf is raised nearly the full length of the leaf. The taxonomic characteristics of *T. baccata* and *T. brevifolia* have been detailed (Bailey, Britton, Den Oudin, Rehdar, Sargent).

A preferred variant or cultivar of *T. baccata* is referred to herein *T. baccata* 'resembling Hessei', meaning a *T. baccata* cultivar which resembles *T. baccata* 'Hessei' as described in Den Oudin. This cultivar is characterized by distinctly thicker leaves than usual for *T. baccata*, with rather stiff and recurved leaves similar to those of Terreya or Cephalotaxus. Specifically the 'Hessei' variant has leaves "rather long and broad, more or less like those of Cepthalotaxus, 30 mm to 35 mm long, 3.5–4 mm broad, some sickle-shaped dark green with a raised midrib above, lighter green beneath".

Taxus plants can be obtained from conventional sources, such as large nurseries. Cultivars of *T. baccata* can be obtained, for example, from Ohio Agricultural Research and Development Center, Secrest Arboretum, 1680 Madison Avenue, Wooster, Ohio, and Arnold Arboretum, 125 Arborway, Jamaica Plain, Mass. *T. baccata* 'resembling Hessei' was obtained from Redwood Nursery, 2800 E1 Rancho Drive, Santa Cruz, Calif. Similar cultivars can be obtained from the Ohio ARDC. The 'resembling Hessei' cultivar is also available from Escagenetics Corporation, 830 Bransten Road, San Carlos, Calif. 94070-3305.

Stem cuttings from Taxus plants are rooted using standard methods, and generally involve contacting the cut portion of the stem with an auxin or auxin-like growth regulator followed by imbedding the cutting in a moist rooting medium. The rooting medium may be soil or other suitable rooting support medium. The cuttings are then maintained in growth chamber or greenhouse under very high humidity conditions, until rooting has occurred. Once rooting has occurred, the plants are acclimatized for planting out of doors by transferring the plants to soil and slowly lowering the humidity level to that encountered in the ambient environment.

Callus initiation begins with the excision of a desired plant body ("explant") from a selected species of Taxus. In general, an explant derived from nearly any plant organ containing growing tissue or meristematic tissue will be capable of giving rise to callus under the culture conditions set forth herein and in Example 2, including shoot tips, root tips, stem cambium and leaves, although stem cambium tissue is preferred.

Prior to callus initiation, explants should be sterilized. Sterilization can be accomplished by immersing the explant in a solution capable of killing surface bacterial, fungal and viral organisms. Any solution having oxidative properties sufficient to kill such agents without significant degradative action on the plant tissue, such as a dilute solution of sodium hypochlorite, is satisfactory.

Callus tissue is initiated by placing the sterilized explant on a solid support medium containing nutrients favorable to callus initiation and growth, and then incubating these cultures under growth conditions, as detailed in Example 2. One optimal medium contains the plant hormones, α-naphthaleneacetic acid (NAA) and 6-benzylamino purine (BAP), sucrose as a physiological carbon source, casein hydrolysate, the vitamins nicotinic acid, thiamine HCl, pyridoxine HCl, and myo-inositol and Gamborg's B5 salts.

It will be appreciated that the specific representatives of a particular type of nutrient described above can be varied. For example, NAA can be substituted by another suitable plant hormone having auxin-like activity and sucrose could be substituted by fructose or a similar monosaccharide. Examples of other suitable salt compositions include Litvay's salts (Verma et al. 1982. Proc. 5th Intern. Congr. Plant Tissue and Cell Culture: 59) or the Durzan & Campbell's salts (Gupta et al. 1985. Plant Cell Reports 4: 177).

The explants may be transferred under sterile conditions several times if callus formation does not occur in the first culture. Callus proliferation and growth can be further stimulated by subculturing initiated callus fragments on fresh medium.

Callus produced in accordance with this invention has the following characteristics: (1) a more or less solid body of parenchymatous cells having an amorphous morphology and generally lacking differentiated vascular or organ tissues and lacking clearly defined meristematic zones; (2) good intercellular adhesion but capable of breaking apart into irregularly sized fragments when mechanically disturbed; and (3) a rate of mass doubling of several weeks to several months.

B. Preparation of Cell Suspension

The callus tissue formed above is cultured in a cell suspension growth medium, to produce a suspension of callus-derived cells. To obtain an actively dividing suspension of cells, callus obtained as above is broken up into small fragments, by mincing, agitation or other suitable method, and is then added to a vessel containing liquid culture medium substantially the same as the solid culture medium described above, except that solidifying agent is omitted (see Example 3). One preferred medium contains the plant hormones, α-naphthaleneacetic acid (NAA) and 6-benzylamino purine (BAP), sucrose as a physiological carbon source, casein hydrolysate, the vitamins nicotinic acid, thiamine HCl, pyridoxine HCl, and myo-inositol and Gamborg's B5 salts. Other suitable media are disclosed above. Such cell-suspension media suitable for forming cell suspensions from cultured callus fragments are also referred to herein, generally, as "cell-suspension growth media".

The vessel containing the callus and culture medium is then agitated, under suitable physical conditions, to achieve formation of the cell suspension. Agitation of the medium has the effect of causing newly formed cells to break apart into finely divided clusters, generally 1–10 cells each, and promotes cell division by maintaining the cells in full contact with hormones, nutrients and other constituents of the culture medium.

The cell suspension is typically cultured in the cell-suspension medium until just before active cell division declines or is halted, generally as a result of nutrient depletion. At such time during active cell growth, a desired aliquot of the cells in the suspension can be transferred to new culture medium, and thus can be subcultured indefinitely, or can be used to form pseudocallus as further described below.

A cell suspension produced as above will have the following characteristics: (1) few-celled clusters of generally 1–10 cells; (2) limited intercellular adhesion; and (3) a rate of mass doubling, in the cell-suspension growth medium, of 7 to 21 days.

The ability of the callus-derived cell suspension, prepared as above, to produce taxane has been investigated in suspension derived from a *T. baccata* and *T. brevifolia*, as detailed in Example 5. Taxane levels in the cell culture medium was examined at 2–4 weeks and 2–7 weeks incubation for suspension cells derived from a *T. baccata* and *T. brevifolia*, respectively. The results, given in Tables III and IV, show only barely detectable levels of taxane (in the few parts per billion fresh weight range). The cell-culture method for taxane production just described closely follows the teaching of U.S. Pat. No. 5,019,504 and Misawa (Misawa, 1982, 1983) for producing taxanes by cell suspensions derived from *T. brevifolia* callus.

More recent studies initiated in support of the present invention show that cell suspensions of *T. baccata* 'resembling Hessei' are capable of producing significantly higher taxane levels in cell suspensions when the cells are subcultured under selected conditions. This result appears to be specific to *T. baccata* cells and the levels of taxanes obtainable from the suspended cells is still more than an order of magnitude lower than that of the present invention.

C. Induction of Pseudocallus

According to an important aspect of the invention, the suspended cells obtained from callus are grown on a support culture medium, to produce a pseudocallus which is characterized by (1) a loose, amorphous aggregation of cells lacking differentiated vascular or organ tissues and lacking clearly defined meristematic zones and (2) very poor intercellular adhesion resulting in extreme tissue friability with the pseudocallus falling apart into numerous individual cells and small cell clusters when mechanically disturbed. In addition, the pseudocallus shows an initial rate of mass doubling on fresh support medium which is significantly greater than that of the initial callus tissue grown on the same support medium.

The support medium includes a solid or semi-solid support capable of supporting the suspended cells in an immobile state in which the cells are in nutrient-exchange contact with, but not submerged in, a cell culture medium. One preferred type of support is a semi-solid support formed by gelling or colloidal agents, such as gums, agar, or Gelrite, a gelling agent produced by bacteria (*Pseudomonas elodea*) containing glucuronic acid, rhamnose and glucose as part of a heteropolysaccharide, available from Kelco (San Diego). Experiments conducted in support of the present invention indicate that an optimal solidifying agent is Gelrite, particularly in comparison with agar. Other suitable supports include filter paper or cell mesh. The mesh may be composed of any suitable, light-weight, physiologically inert substance, such as a polymer plastic. A preferred mesh is a microporous polypropylene membrane raft produced by Sigma (St. Louis, Mo.).

The medium in the support culture medium is preferably substantially the same as the suspension culture induction medium, except for the additional presence (in a semi-solid support medium) of gelling agents. One preferred medium contains the plant hormones, 60-naphthaleneacetic acid (NAA) and 6-benzylamino purine (BA), sucrose as a physiological carbon source, the vitamins nicotinic acid, thiamine HCl, pyridoxine HCl, and myo-inositol and Gamborg's B5 salts. In the case of pseudocallus produced on filter paper or microporous mesh, the medium will not contain the solidifying agent.

In order to promote rapid and efficient production of pseudocallus, it is advantageous to plate the cells from the cell suspension densely so as to ensure that the individual cells and cell clumps are substantially in contact with one another. If the plated cells are too widely spaced, little or no growth may occur, possibly the result of early senescence of the cell culture.

Preferably, the cells are cultured in the absence of light at about room temperature (24° C.). Pseudocallus development, i.e., appearance of an amorphous aggregation of cells, is usually seen within 4–14 days. With continued culturing, the pseudocallus cells will undergo a mass doubling typically in 2–4 weeks, and in some cases, as short as seven days. This rate of mass doubling is significantly higher than that of the initial callus tissue cultured on the same medium, where doubling times of several weeks to several months are observed.

FIG. 1A shows the increase in cell mass (circles) of suspension cells derived from *T. baccata* 'resembling Hessei' and cultured on semi-solid culture medium, as detailed in Example 5. The appearance of cells characteristic of pseudocallus was observed within the first two weeks, after which cell mass more than doubled in the next two weeks. The plateau in cell mass observed at about 4 weeks may represent a shortage in cell nutrients, since the pseudocallus can be stimulated to new cell mass increase by subculturing on fresh support medium.

Figure 1B:
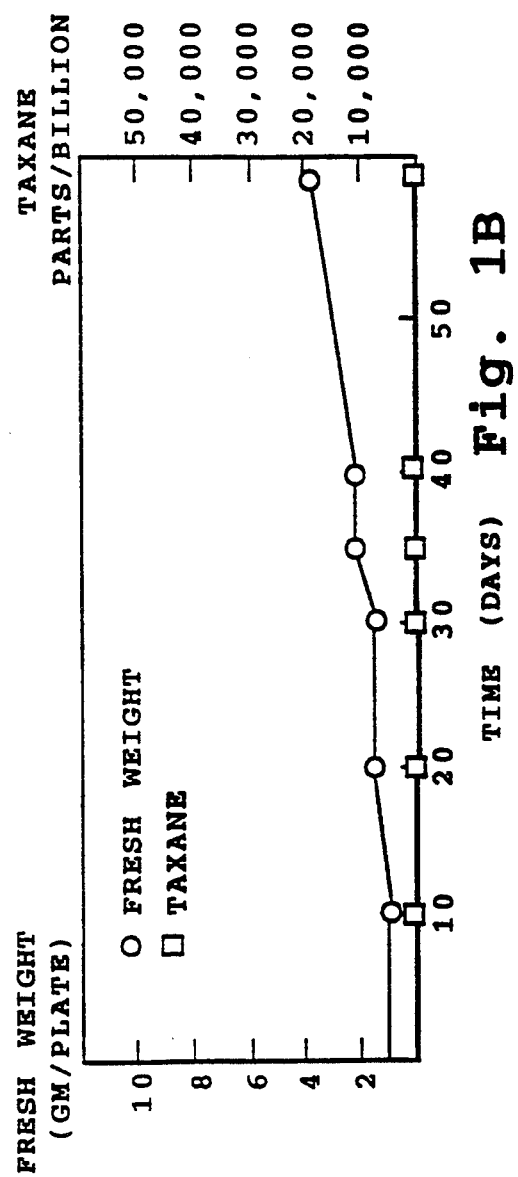
Figure 1B shows a time course of pseudocallus growth (squares) and pseudocallus taxane production (circles) from a cell line of *T. brevifolia*.

FIG. 1B shows the increase in cell mass (circles) of suspension cells derived from *T. brevifolia* and cultured on semi-solid culture medium, as above. Again, the appearance of cells characteristic of pseudocallus was observed within the first two weeks, although cell doubling required about 5–6 weeks.

The invention includes, in one aspect, pseudocallus derived from explants of a species of Taxus, characterized by (a) a loose, amorphous aggregation of undifferentiated Taxus cells without substantial intercellular adhesion; and a rate of mass doubling, when the cells are grown on fresh support culture medium, which is significantly greater than that of callus cells grown under the same conditions.

The pseudocallus is preferably produced, as detailed above, by the steps of (a) providing fragments of callus tissue induced from Taxus explants; (b) culturing the fragments under cell-suspension growth conditions, to produce a suspension of callus-derived cells; (c) plating the cells of the suspension on a support culture medium; and (d) allowing the plated cells to divide on the support culture medium to form the pseudocallus, where the rate of mass doubling of the cells on the culture medium is significantly greater than that of callus tissue obtained from the same Taxus species grown on the same medium.

One preferred pseudocallus, for use in taxane production, is derived from *T. baccata* 'resembling Hessei'. As will be seen below, pseudocallus derived from this source is capable of producing high levels of taxane when grown on the support culture medium. An exemplary pseudocallus from this source is obtained from a suspension of cells deposited with the Escagenetics Corporation, 830 Bransten Road, San Carlos, Calif. 94070-3305, and identified as Escagenetics Cell Line 90T1.

II. Production of Taxanes

This section describes the de novo synthesis of taxanes from pseudocallus obtained from *T. baccata* callus tissue. As the term is used herein, "taxanes" means taxol or taxol together with related diterpene derivatives of taxol which contain an alkaloid-like taxane ring and which are produced naturally in Taxus species plants. Where taxane amounts are given in units of μg/g fresh weight of tissue, as determined by the ELISA assay detailed in Example 7, "taxanes" specifically means taxane species, including taxol, which are immunoreactive with the assay antibody. The structure of taxol and some related taxane-ring alkaloid derivatives obtained from *T. brevifolia* plants is discussed for example by Huang et al., referenced above.

In order to achieve de novo synthesis of taxanes in pseudocallus, pseudocallus cells derived from *T. baccata* are cultured on the above support culture medium until a desired level of taxanes is achieved. In particular, the medium to which the pseudocallus is in nutrient-exchange contact includes at least one physiological carbon source, salts, vitamins and at least one plant growth regulator. These nutrients may be supplied by any conventional plant tissue culture medium, although a preferred production medium is described in Example 6A.

The effect of both the carbon source and the plant growth regulators on taxane production can be assessed by conventional methods. Although sucrose is the preferred carbon source and NAA and BA are the preferred auxin and cytokinin growth regulator sources, these components can be systematically supplemented or replaced with other carbon sources or hormones in order to examine their effects on production.

Casein hydrolysate is a common constituent of tissue culture media and is used herein both in the callus culture medium and in the cell suspension culture medium. It has been learned in experiments conducted in support of the present invention, and discussed in Example 6C, that the presence of casein hydrolysate in the taxane production medium seems to suppress taxane production as compared with media omitting casein hydrolysate. Thus, it is preferable to omit casein hydrolysate from the production medium and in instances where a single medium is being used both for pseudocallus induction and for taxane production.

In addition to culture medium parameters, other aspects of the physical environment appear to affect taxane production. Low levels of atmospheric carbon dioxide and removal of ethylene and related compounds may promote taxane production i.e., where culturing is carried out in an atmosphere which is substantially free of ethylene and has a sub-atmospheric concentration of $CO_2$. These conditions can be met by culturing the pseudocallus in an enclosed growth chamber that is provided with aqueous solutions or pellets of NaOH and $KMnO_4$ that are open to the atmosphere of the growth chamber. The water in these solutions helps to maintain high humidities while the NaOH and $KMnO_4$ in solution act as absorbants for $CO_2$ and ethylene respectively. It will appreciated, therefore, that the vessels containing pseudocallus undergoing taxane production should be covered in such a way that carbon dioxide and ethylene can escape from the culture vessel into the growth chamber where they can be removed by the absorbants.

Photoperiod and temperature may also affect taxane production. Good production levels have been achieved when pseudocallus is cultured at lower temperatures, generally below 25° C., and in the absence of light, as illustrated in Example 6B. It will be recognized that other physical parameters, such as pH of the production medium may also affect taxane production.

FIG. 1A shows a plot of taxane production in *T. baccata* 'resembling Hessei' pseudocallus on a semi-solid support medium, as detailed in Example 6. Taxane levels were measured using an ELISA antibody taxane diagnostic kit supplied by Hawaii Biotechnology Group, Inc (Aila, HW), as outlined in Example 7. (Here taxane levels are defined as the level of taxanes which are immunoreactive with the ELISA antibody). Briefly, pseudocallus cells were rinsed, weighed, and disrupted in methanol to release intracellular taxane. The solution-phase material was then assayed by the ELISA antibody method.

As seen in FIG. 1A, taxane production occurs most actively after the pseudocallus cells have reached a plateau in mass growth, presumably because the precursor metabolites necessary for taxane production are being synthesized and are accumulating during the most active growth phase, or because taxane production is inherently more active in non-growing cells, or a combination of these factors. The final level of cellular taxane produced in the FIG. 1 study was about 50 $\mu$g taxane/g fresh weight pseudocallus tissue, also expressed as $5 \times 10^4$ parts per billion.

The difference in taxane production ability between pseudocallus derived from *T. baccata* and *T. brevifoli* apparent from FIG. 1B, which shows (circles) levels intracellular taxane produced in *T. brevifolia* cells. These levels of taxanes in *T. brevifolia* cells remained at the threshold of detection level (a few parts per billion) through the period of pseudocallus culture on the support medium.

According to one aspect of the invention, there is provided a method for taxanes (including taxol) production which involves, first obtaining from explants of *Taxus baccata*, and preferably *T. baccata* 'resembling Hessei' pseudocallus of the type described above. The pseudocallus is cultured on a support culture medium until a selected level of taxanes is produced in the cells. Preferably the selected level of taxanes which is reached is at least about 25 $\mu$g taxanes/g wet weight of pseudocallus tissue.

In another aspect, the invention includes cultured cells derived from Taxus plant tissue, and containing least 25 $\mu$g taxanes/g fresh weight of cells. As seen FIG. 1A, the cells may contain up to 50 $\mu$g taxane/g fresh weight of cells.

III. Taxane Compositions

This section discusses methods according to the invention for extracting, purifying and identifying taxanes produced by pseudocallus cell mass as described above.

A. Extracting Taxanes

Taxanes produced within Taxus pseudocallus remain substantially sequestered within the cells of the pseudocallus, as opposed to secreting into the culture medium as occurs in some plants. Thus, taxane production requires the harvesting and destruction of the pseudocallus in order for the taxanes to be extracted and purified.

Extraction can be accomplished using conventional methods well known in the art. Because taxol and other taxanes are hydrophobic molecules that are poorly soluble in water, extraction is best achieved using organic solvents. In a typical extraction method, pseudocallus cell mass is homogenized and extracted with a low molecular weight alcohol, such as methanol or ethanol. The alcohol extract is then shaken with a two-phase water/chloroform mixture to extract the taxane predominantly into the lower chloroform phase (Huang, Wani).

In another extraction procedure, the pseudocallus are first air dried and then extracted with methanol. The taxane in the methanol extract is then extracted into the chloroform phase as above. This extraction procedure is detailed in Example 7.

B. Identification and Characterization of Culture-Produced Taxanes

Figure 2A:
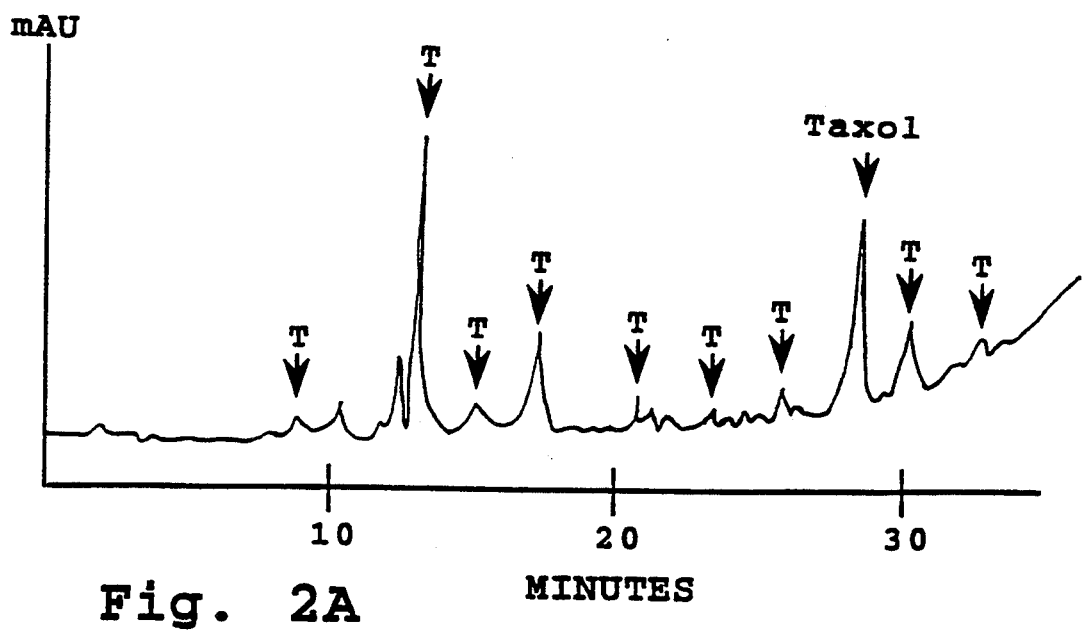
FIG. 2A is an HPLC chromatogram of taxanes, including taxol, produced by leaf tissue derived from *T. baccata*.
Figure 2B:
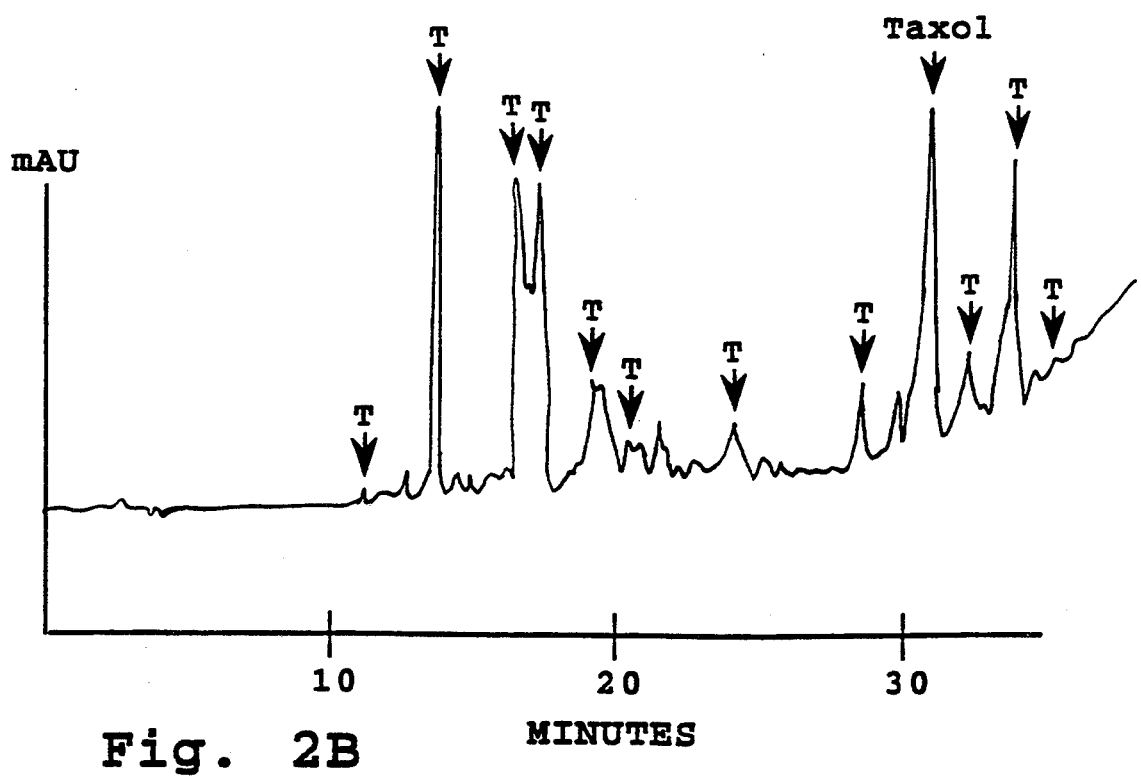
FIG. 2B is an HPLC chromatogram of taxanes, including taxol, produced by pseudocallus of *T. baccata*.

The taxane extract from pseudocallus culture can be separated and purified into its individual components using standard chromatographic techniques, such as HPLC, as detailed in Example 7. FIG. 2B shows an HPLC chromatogram of a typical taxane extract from pseudocallus according to the invention, as detailed in Example 7. As seen, the composition includes a taxol peak and several other peaks constituting related taxanes (indicated by "T"). In addition, the composition contains a number of other unidentified peaks. For purposes of comparison, the HPLC profile of taxanes obtained from leaf tissue is shown in FIG. 2A. Three of the taxanes peaks, in FIGS. 2A and 2B are common to both leaf and culture-produced samples. One peak has been identified as taxol, as confirmed below.

HPLC analysis provides a convenient method for following changes in taxane composition of pseudocallus extract as may occur with changes in culture medium and culture conditions, as well as for identifying differences between cell lines of different genotypes. Thus, it is possible not only to characterize the nature of the extract produced, but also to use such data to select particular cell lines that are high producers of taxol. HPLC chromatography is also a simple means of separating and purifying desired taxane components, such as taxol.

Aside from the general methods described above for identifying taxanes as a group, specific methods can be used to test for the presence of taxol in an extract or to confirm the identity of taxol in a peak of a chromatographic profile.

Figure 3A:
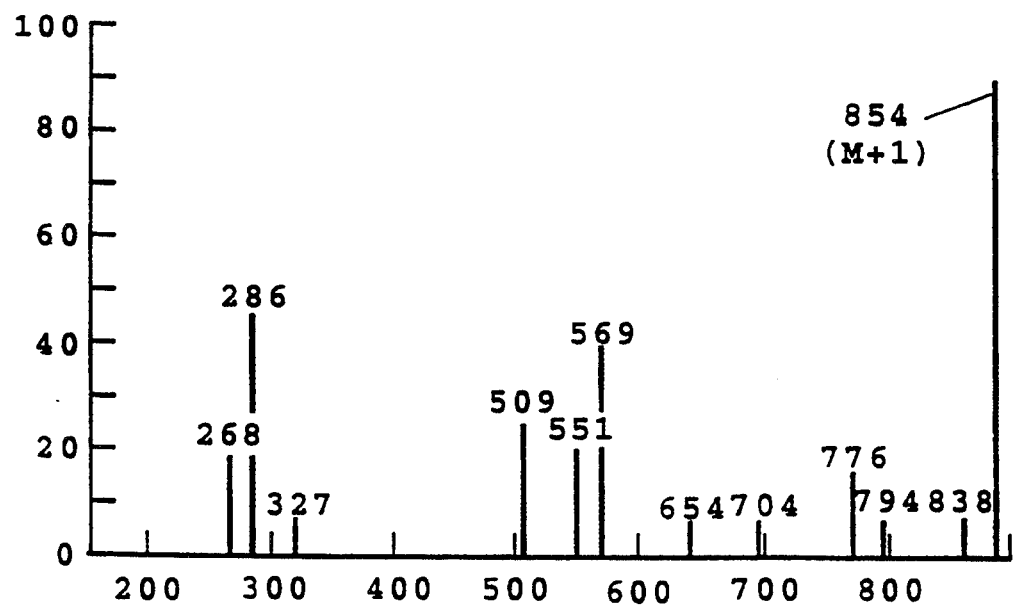
FIG. 3A is a mass spectra of a standard taxol sample.
Figure 3B:
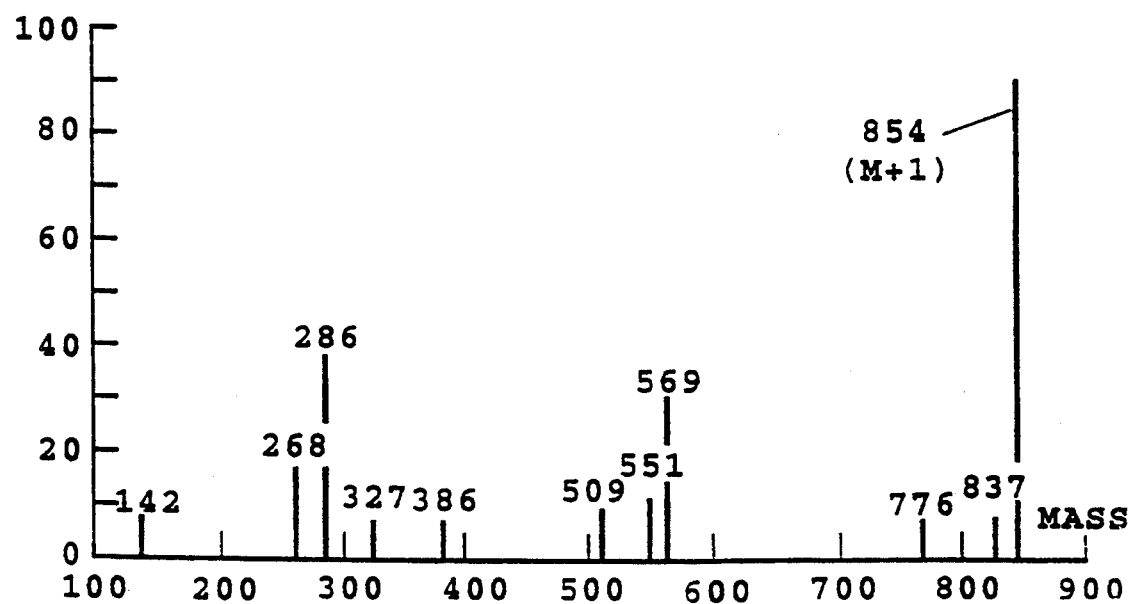
FIG. 3B is a mass spectra of taxol produced in cell culture, in accordance with the present invention.

The identity of purified, culture-produced taxol can be further confirmed by mass spectroscopy, as described in Example 8. FIGS. 3A and 3B show the mass spectra of a standard taxol sample and a taxol sample purified from pseudocallus culture, in accordance with the invention. As discussed in Example 8, the spectra contain several common fragment ions which are predicted from taxol fragmentation, including fragment masses of 268, 286, 327, 509, 551, and 569.

Taxane production, and the presence of taxol, can be further examined by bioactivity tests, such as have been described (Rowinsky). In one bioactivity test, the presence of a taxol-like compound is confirmed by its ability to promote polymerization of tubulin and inhibit the depolymerization of microtubules. In this detection method, microtubules are isolated according to conventional methods and are treated with a taxol standard and the sample to be tested. The rate of microtubule assembly in the presence of the standard is then compared to the rate determined for the sample to determine if the sample has taxol-like properties.

From the foregoing, it can be appreciated how various objects and features of the invention have been achieved. A novel tissue culture cell type, the pseudocallus, has been produced that is capable of de novo production of significant amounts of taxol, in general as great or greater than the concentrations of taxol produced in the stem and leaf tissue of the same species from which the pseudocallus is derived. In particular, it has been discovered that pseudocallus of cell lines derived from the species T. baccata is a high producer of taxol, notwithstanding the relatively low levels of taxol present in stem and leaf in this species.

The following examples illustrate various methods of preparing pseudocallus tissue for producing taxanes, culture conditions necessary to achieve production and methods for extracting and characterizing taxanes from the pseudocallus, and are intended to illustrate, but not limit, the scope of the invention.

EXAMPLE 1

Propagation of Taxus Plants

Individuals of T. brevifolia were obtained from a commercial nursery and from wild populations in Washington and Oregon. A plant identified as T. baccata 'resembling Hessei', as described above, was obtained from a commercial nursery in Santa Cruz, Calif. These plants were planted out of doors in a standard soil mix comprising redwood compost, peat moss and sand. Plants were watered twice weekly. A dilute, general purpose fertilizer was applied once weekly at watering time.

Individuals were propagated by stem cuttings. Terminal segments 4–6 inches of stems from individuals of each species were excised by cutting the stem cleanly at an approximate 45° C. angle to provide expanded exposure of stem cambium on the cuttings.

The bases of the cuttings were treated with Hormodin3 ®, a powdered rooting composition containing a plant hormone with auxin-like activity to promote root formation. The treated cuttings were then basally inserted into a peat-Perlite ® e growth medium having a pH of 6.0. During root initiation and growth, the cuttings were maintained in conditions of high humidity and away from direct contact with sunlight. Root formation occurred after culturing at 25° C. for approximately 45 days. Cuttings were made from July to September.

After root formation, the cuttings were transferred to a standard potting soil mix and acclimatized to lower humidity levels.

EXAMPLE 2

Callus Induction Method 1

Fully expanded, but not yet hardened, flushes of new growth were excised from the shoot tips of cultivated plants of T. baccata and T. brevifolia, and surface sterilized in a 1% sodium hypochlorite solution followed by 3 rinses with sterilized, deionized water. The flushes were cut into smaller stem segments, 2–5 mm long, and cultured horizontally on a solid callus induction medium having the composition set forth in Table 1 in the absence of light and at a temperature of about 24° C.

TABLE 1

| Composition of Callus Induction & Culture Medium* | |
|---|---|
| Component | Concentration |
| Salts (Gamborg's B5) | 3.6 mg/L |
| Vitamins | |
| nicotinic acid | 0.5 mg/L |
| thiamine HCl | 0.1 mg/L |
| pyridoxine HCl | 0.1 mg/L |
| myo-inositol | 100 mg/L |
| Sucrose | 30 gm/L |
| NAA | 10 µM |
| BAP | 0.2 µM |
| Casein hydrolysate | 500 mg/L |
| Gelrite ® | 2 gm/L |

*pH adjusted to 5.8

After about 4 weeks in culture, at 24° C. and in the absence of light, 100% of the segments showed callus formation. Callus culture was allowed to continue until individual callus bodies reached about 2 mm in diameter. At this point, the callus tissue was fragmented and transferred to new callus growth medium for further callus proliferation or was utilized in the formation of cell suspension cultures.

Callus Induction Method 2

Leaves were removed from newly flushed stem tips of *T. baccata* and *T. brevifolia*, and surface sterilized in a 1% sodium hypochlorite solution followed by 3 rinses with sterile deionized water. The leaves were cut into smaller segments, 2–5mm long, and cultured individually on a solid callus induction medium having the composition set forth in Table 1.

After about 4 weeks in culture, at 24° C. in the and in the absence of light, 50% of the explants showed callus formation. Callus culture was allowed to continue as described in the callus induction method 1, set forth immediately above.

EXAMPLE 3

Production of Taxus Cell Suspension

Callus tissue of both *T. baccata* and *T. brevifolia* obtained in Example 2 was transferred whole or fragmented, either by teasing the tissue apart or by mincing the tissue with a sharp blade, into small pieces approximately 2 mm in diameter and transferred aseptically to 125 ml Erlenmeyer flasks containing about 10 ml of liquid culture medium A that was identical in composition to the callus induction medium described in Table 1, except that the solidifying agent, Gelrite®, was omitted and selected component concentrations were altered to the values set forth in Table 2.

TABLE 2

Selected Component Concentrations in Liquid Culture Medium A

| Component | Concentration |
|---|---|
| Vitamins | |
| nicotinic acid | 0.5 mg/L |
| thiamine HCl | 1.0 mg/L |
| pyridoxine HCl | 0.5 mg/L |
| myo-inositol | 100 mg/L |
| BAP | 0.1–0.2 µM |

The flasks were covered with a sterile cap and cultured in low levels of ambient room light, at about 24° C. for about 14–21 days, during which time the flasks were continuously agitated to swirl the callus fragments in the liquid culture medium. During this treatment, the callus fragments gradually became reduced in size, and an actively dividing suspension of individual cells and cell clusters of generally less than 10 cells each was created.

Good growth of cell suspension cultures were also achieved on an alternative liquid growth medium B. Liquid growth medium B is identical to the callus induction medium described in Example 2, except that Gamborg's Salts have been substituted with the salt composition of Table 2A, the vitamin composition of Table 2B, and the trace element compositions noted in Tables 2C and 2D.

TABLE 2A

Salt Composition of Liquid Culture Medium B

| Component | Amount/Liter |
|---|---|
| Ca(NO$_3$)$_2$—4H$_2$O | 3.5 mM |
| MgSO$_4$—7H$_2$O | 1.2 mM |
| NaH$_2$PO$_4$—H$_2$O | 2.0 mM |
| KNO$_3$ | 16 mM |
| KCL | 14 mM |
| KI (1000×) (75 mg/100 ml) | 1 ml |
| Na$_2$SeO$_3$ (1000×) (18.3 mg/L) | 1 ml |
| Fe-Citrate (200×) † (Table 2D) | 5 ml |
| Trace Element 3 (1000×) (Table 2C) | 1 ml |

† added from a sterile stock solution after media is autoclaved

TABLE 2B

Vitamin Composition of Liquid Culture Medium B †

| Vitamin | Amount/500 ml |
|---|---|
| Thiamine-HCl | 1000 mg |
| Nicotinic Acid | 500 mg |
| p-Aminobenzoic acid | 50 mg |
| myo-Inositol | 5000 mg |
| Pyridoxine-HCl | 250 mg |
| Choline-Cl | 2500 mg |
| D-Biotin | 0.5 mg |
| Cyanocohalamin | 0.55 mg |
| Folic Acid | 5 mg |

† (1000×)

TABLE 2C

Trace Element Composition of Liquid Culture Medium B †

| Trace Element | Amount/500 ml |
|---|---|
| Na$_2$EDTA | 8591 mg |
| NH$_4$VO$_3$ | 23 mg |
| CuSO$_4$ 5H$_2$O | 19.6 mg |
| NiSO$_4$ 5H$_2$O | 44.8 mg |
| CoCl$_2$ 6H$_2$O | 81.1 mg |
| MnCl$_2$ 4H$_2$O | 14.7 mg |
| Na$_2$MoO$_4$ 2H$_2$O | 387.7 mg |
| H$_3$BO$_3$ | 2002.4 mg |
| ZnSO$_4$ 7H$_2$O | 1100.8 mg |
| CrK(SO$_4$)$_2$ 12H$_2$O | 97.8 mg |
| FeSO$_4$ 7H$_2$O | 1244.2 mg |

† (1000×) pH adjusted to 3.5 prior to autoclaving

TABLE 2D

200 × Fe Citrate Solution of Liquid Culture Medium B

| Trace Element | Amount/500 ml |
|---|---|
| Na$_3$ Citrate 2H$_2$O | 2.94 g |
| Fe SO$_4$.7H$_2$O | 2.78 g |

Adjust pH to 4.5–4.8 and autoclave.

EXAMPLE 4

Induction of Taxus Pseudocallus

The aliquots of the cell suspensions of both *T. baccata* and *T. brevifolia* produced in Example 3 were removed by pipette, transferred to a Buchner funnel and the liquid culture medium removed under vacuum to leave behind the cells from the suspension. The cell density in the liquid suspension could then be calculated.

Cells from suspension were then plated on a pseudocallus culture medium identical to the callus induction medium described in Example 2 and Table I, except that casein hydrolysate was omitted. After plating, all traces of the standing liquid were removed so that the cells would not become asphyxiated.

The suspension was plated densely enough to ensure that the individual cells and cell clusters were in substantial contact with one another, generally 1000 to 2000 mg of fresh weight cells per standard 100×25 mm petri dish, containing 50 ml of medium. The plated cells were cultured in the absence of light at a temperature of 24° C.

After about 14 days in culture, pseudocallus development was evident. Growth continued at a rate sufficient to result in a doubling of the mass of the pseudocallus within 3 to 4 weeks (earlier for later examples). At this point, the pseudocallus was either divided up for further subculture, or was dedicated to taxane production.

EXAMPLE 5

Taxane Production in Cell Suspensions

The cell suspensions derived from *T. baccata* and *T. brevifolia*, produced in accordance with Example 3, were carried through a series of subcultures. Taxane production was assayed periodically by an ELISA assay of isolated material, as described in Example 7 below. Taxane production in a *T. brevifolia* cell suspension is reported in Table 3. Taxane production in a *T. baccata* cell suspension is reported in Table 4.

TABLE 3

Taxane Production in Cell Suspensions of *Taxus brevifolia*

| Age of Suspension | Taxanes* |
|---|---|
| 2 Weeks | 2.2 |
| 3 Weeks | 0.5 |
| 4 Weeks | 4.3 |

*parts per billion fresh weight

TABLE 4

Taxane Production in Cell Suspensions of *Taxus baccata*

| Age of Suspension | Taxanes* |
|---|---|
| 2 Weeks | 2.1 |
| 3 Weeks | 2.3 |
| 4 Weeks | 9.9 |
| 5 Weeks | 1.1 |
| 6 Weeks | 3.9 |
| 7 Weeks | 2.8 |

*parts per billion of fresh weight

These results demonstrate that de novo production of taxanes in cell suspensions is quite low, in the parts per billion range. It is not known whether this level of measured taxane represents taxanes synthesized in culture, or residual taxanes from the starting plant material.

EXAMPLE 6

Taxane Production in Pseudocallus

A. Effect of Taxus plant Source

Pseudocallus derived from stem explants of *T. baccata* and *T. brevifolia*, produced in accordance with Example 4, were subcultured on a taxane production medium identical to the pseudocallus growth medium therein described in the absence of light and at a temperature of 24° C. The cultures were assayed periodically for taxane content, the results of which are reported in Table 5. These results, in combination with change in fresh weight of the pseudocallus over the same period, are graphically depicted in FIGS. 1A and 1B.

TABLE 5

Taxane Production in Pseudocallus Cultures of *Taxus baccata* and *Taxus brevifolia*

| | Concentration of Taxanes* | | |
|---|---|---|---|
| Age of Culture | baccata I | baccata II | brevifolia |
| 0 Weeks | 2 | 2 | 3 |
| 3 Weeks | 22 | 14 | <0.5 |
| 4 Weeks | 2,678 | 50 | 8 |
| 5 Weeks | 12,875 | 695 | 6 |
| 6 Weeks | 59,350 | 1105 | 6 |
| 7 Weeks | 61,700 | — | — |

TABLE 5-continued

Taxane Production in Pseudocallus Cultures of *Taxus baccata* and *Taxus brevifolia*

| | Concentration of Taxanes* | | |
|---|---|---|---|
| Age of Culture | baccata I | baccata II | brevifolia |
| 8 Weeks | 10,433 | 7816 | 12 † |

*parts per billion fresh weight
† pseudocallus of *T. brevifolia* died after 8 weeks in culture B. Effect of Light Regime Pseudocallus was induced from stem explant suspension cells of *T. baccata*, in accordance with Example 4, and was divided into two samples each on a taxane production medium identical to the pseudocallus growth medium therein described, except that 0.2 µM BA was used. Culture B was incubated at 24° C. in the absence of light. Culture A was incubated at 24° C. under a light regime of 16 hours of light (200 footcandles at a distance of 24 cm, supplied by a Cool White ® fluorescent light lamp supplied by General Electric Corporation) alternated with 8 hours of darkness. The cultures were periodically assayed for taxane content. The results are reported in Table 6.

TABLE 6

Effect of Light on Taxane Production

| | Taxane Concentration † | |
|---|---|---|
| Day No. | Culture A (light) | Culture B (no light) |
| 0 | 3 | 3 |
| 14 | 1 | 1 |
| 20 | 13 | 22 |
| 28 | 890 | 2,234 |
| 35 | 801 | 12,875 |
| 41 | 985 | 59,350 |

† parts per billion of fresh weight

C. Effect of Casein Hydrolysate

Pseudocallus was induced from stem explant suspension cells of *T. baccata*, in accordance with Example 4, and was divided into two samples, Culture A and Culture B, each of which was plated on a taxane production medium identical to the pseudocallus growth medium therein described, except that casein hydrolysate was absent in the culture medium of Culture A and present from the culture medium of Culture B. The cultures were incubated under identical conditions at 24° C. and in the absence of light. The cultures were assayed periodically for taxane content. The results are reported in Table 7.

TABLE 7

Effect of Casein Hydrolysate on Taxane Production

| | Taxane Concentration † | |
|---|---|---|
| Day No. | Culture A (no casein hydrolysate) | Culture B (casein hydrolysate) |
| 0 | 3 | 3 |
| 14 | 1 | 1 |
| 20 | 22 | 34 |
| 28 | 2,234 | 2,784 |
| 35 | 12,875 | 6,286 |
| 41 | 59,000 | 19,850 |

† parts per billion of fresh weight

EXAMPLE 7

HPLC Characterization of Taxane Compositions

A. Taxol Extraction

Typically about 10 needles from *T. brevifolia* (0.1–0.2 g f. wt.) or washed cells from tissue culture (0.1–0.2 g f. wt.) were homogenized in 10 ml methanol (leaf material) or 2 ml methanol (tissue culture samples) using an Ultra Turrax homogenizer. Extracts were centrifuged (5 min in a bench top clinical centrifuge) and 10% of the supernatant prepared for ELISA assays and 90% for HPLC analysis. The ELISA, which detects taxol, cephalomanine and to a less extent some other related taxanes, was used as a screen to detect samples containing significant levels of taxol like taxanes. Samples thus identified were subjected to HPLC analysis.

B. ELISA Assay

The crude supernatant from above was evaporated to dryness and the residue was partitioned between 0.5 ml of water and 0.5 ml of $CH_2Cl_2$. The aqueous layer was discarded and the organic fraction reduced to dryness and then redissolving in 100 ul of methanol. Taxol-like cross reactive taxanes were determined using reagents supplied by Hawaii Biotechnology Group (Aiea, HW) using Immulon II microtiter plates from Dynatech and a goat anti-rabbit alkaline phosphatase conjugate from CalTag. The ELISA, which is a competitive inhibition assay, was carried out essentially according to the suppliers instructions. Results are presented as $\mu g/ml$ on the basis of a pure taxol standard (N.C.I.).

C. HPLC Analysis

The crude supernatant was evaporated to dryness and the residue partitioned between 2 ml of water and 2 ml of $CH_2Cl_2$. The aqueous layer was discarded and the organic fraction applied to a Bond Elut $NH_2$ SPE cartridge (Varian or Alltech) and eluted with 2×2 ml portions of $CH_2Cl_2$ (discarded). The taxol fraction was obtained by elution with 2×2 ml of 15% methanol in $CH_2Cl_2$. This eluate was evaporated to dryness and redissolved in 50–100 ul methanol. HPLC analysis of 10 or 20 ul fractions of this preparation was according to one or other of the following systems and by comparison to authentic standards.

TABLE 8

| System I | |
|---|---|
| Instrument: | HP1090M |
| Column: | Econosphere CN 5µ, 250 × 4.6 mm, dp = 5µ (Supelco) |
| Mobile Phase: | A = MeOH: $CH_3CN$: $H_2O$ (20:5:75) B = MeOh: $CH_3CN$: (20:80) |
| Gradient: | 100% A for 2 minutes, then to 50% B in 48 minutes |
| Temperature: | 40° C. |
| Detector: | DAD, 227 nm |
| System II | |
| Instrument: | HP1090M |
| Column: | Supelcosil LC-18, 250 × 4.6, mm, dp = 5µ (Supelco) |
| Mobile Phase: | A = MeOH: $CH_3CN$: $H_2O$ (20:5:75) B = MeOH: $CH_3CN$ (20:80) |
| Gradient: | From 100% A to 100% B in 50 min. |
| Temperature: | 40° C. |
| Detector: | DAD, 227 nm |

D. Chromatographic Comparison of T1 Leaf and pseudocallus Extracts

Chromatographic profiles of T1 (*T. baccata* 'resembling Hessei') leaf and pseudocallus extracts are shown in FIGS. 2A and 2B, respectively. As shown in the figures, 20 components with taxane-like spectra were detected in the pseudocallus extract and 12 components were detected in the leaf extract (indicated as T in FIG. 1). Only 3 of the taxane-like components occurred in both leaf and pseudocallus extracts (as determined by retention time and spectral data). Those components common to both extracts are shown, in FIGS. 2A and 2B. The peak identified as taxol is indicated.

EXAMPLE 8

Characterization of Culture-Produced Taxol Compositions

A. Mass Spectral Features

A taxol standard was obtained from the National Cancer Institute, Bethesda, Md.

Culture-produced taxol was obtained by extraction from pseudocallus, as above, and purification by chromatography on cyano bonded phase (HPLC system #1) and $C_{18}$-reverse phase (HPLC system #2) columns. The isolated compound (140 ug) was chromatographically pure.

FAB-MS/MS spectra were determined. The spectra of the taxol standard and culture-produced taxol are shown in FIGS. 3A and 3B. In general, good agreement is seen between the spectra for the sample and the standard. Due to the higher signal intensity of the standard spectra (i.e., higher signal to noise ratio) several ions are present in the standard spectra which are not detected in the sample spectra (e.g., 654, 704, 794 and 836).

The sample spectra shows good correlation to the standard spectra with the exception of the trace ions as noted above.

NMR Features

Proton NMR was performed on samples of the standard and culture-produced taxol. For both cases, the following chemical shift lines were observed:

$^1$H-NMR ($CDCl_3$): 1.12 (s, C-17), 1.66 (s, C-19), 1.78 (s, C-18), 2.25 (s, OAc), 2.40 (s, OAc), 2.6 (m, C-14), 3.82 (d, 8, C-3), 4.20 (d, 8, C-20), 4.25 (d, 8, C-20), 4.41 (m, C-7), 4.80 (d, 2, C-2'), 4.96 (d, 4, C-5), 5.72 (d, 8, C-2), 5.80 (dd, 3, C-3'), 6.24 (t, C-13), 6.98 (d, 9, N—H), 7.4 (m, 2-OBz, 3'-OBz, 3'-Ph), 7.7 (m, 3'-OBz).

Although the invention has been described with respect to particular methods and compositions, it will be apparent that various changes and modifications may be made without departing from the invention.

It is claimed:

1. A method for obtaining pseudocallus cell aggregations from explants of a selected species of Taxus comprising the steps of:
   (a) providing fragments of callus tissue induced by culture from Taxus explants containing meristematic tissue physically supported on a support culture medium containing as an auxin, alph-Napthaleneacetic acid (NAA), and as a cytokinin, 6-benzylamino purine (BAP)
   (b) culturing said callus tissue fragments in an aqueous cell-suspension growth medium containing said auxin and said cytokinin to produce a suspension of a plurality of clusters of 1-10 cells having limited intercellular adhesion;

(c) plating cells removed from said cell suspension onto a support culture medium containing said auxin and said cytokinin, said medium capable of physically supporting growth of the cells on a surface thereof; and (d) growing said plated cells on said support culture medium of step (c) to form pseudocallus cells, said pseudocallus cells being a loose, amorphous aggregation of cells lacking differentiated vascular or organ tissues and lacking clearly defined meristematic zones, said cell aggregation having poor intercellular adhesion, extreme friability, and falling apart into numerous individual cells and small cell clusters when mechanically disturbed, said pseudocallus cells showing an initial rate of mass doubling on fresh cell growth medium that is greater than the mass doubling of callus tissue of step (a), and exhibiting the property of producing higher levels of taxanes than that produced by callus tissue of step (a).

2. The method of claim 1, wherein said growing step (d) occurs in the absence of light and in the absence of a taxanes production-inhibiting concentration of casein hydrolysate.

3. The method according to claim 1, wherein the selected species of Taxus is *T. baccata* 'resembling Hessei'.

4. The method of claim 1 wherein said growing step (d) is maintained until a concentration of taxanes in said pseudocallus cells aggregation is at least about 25 μg taxanes/g of said pseudocallus cells.

5. The method according to claim 1 wherein, said support for the culture medium is a solid or semi-solid and is further selected from the group consisting of a gelling agent Gelrite®, agar, filter paper, cell mesh, and a micro-porous polypropylene membrane raft, and combinations thereof.

6. Pseudocallus cells produced by the method of claim 1 from explants of a species of Taxus on a support culture medium containing said auxin and said cytokinin.

7. The pseudocallus cells of claim 6, wherein the species of Taxus is *T. baccata*.

8. The pseudocallus cells of claim 7, wherein the species is *T. baccata* VAR. 'resembling Hessei'.

9. The pseudocallus cells of claim 6 containing at least 25 μg taxanes/g of the pseudocallus cells.

10. The pseudocallus cells of claim 9, which contain at least 50 μg taxanes/g of the pseudocallus cells.

11. The method according to claim 6 wherein, said support for the culture medium is a solid or semi-solid and is further selected from the group consisting of a gelling agent, Gelrite®, agar, filter paper, cell mesh, and a micro-porous polypropylene membrane raft, and combination thereof.

12. A method of de novo production of taxanes in pseudocallus cell culture from Taxus-derived cells comprising the steps of:

(a) selecting callus cells grown from an explant containing meristematic tissue derived from a Taxus plant by culturing said explant physically supported on a support culture medium in the presence of both NAA, as an auxin, and BAP, as a cytokinin;

(b) culturing the selected callus cells from step (a) in an aqueous cell suspension growth medium containing both said auxin and said cytokinin until a suspension of cells in said suspension growth medium is formed, said cell suspension having clusters of from 1-10 cell, limited intercellular adhesion, and a cell mass doubling rate on the order of from about 7 to about 21 days;

(c) transferring the cells of said cell suspension onto a support culture medium capable of physically supporting said transferred cells on a surface thereof, said transfer of said cells occurring before active cell division halts in said culturing step (b);

(d) growing said cells transferred in step (c) on said support culture medium of step (c) in the presence of both said auxin and said cytokinin, to form pseudocallus cells, said pseudocallus cells formed being a loose, amorphous aggregation of cells lacking differentiated vascular or organ tissues and lacking clearly defined meristematic zones, said cell aggregation having poor intercellular adhesion, extreme friability, and falling apart into numerous individual cells and small cell clusters when mechanically disturbed, said pseudocallus cells further having a characteristic of an initial rate of mass doubling on the support culture medium greater than the mass doubling of said callus cells in step (a);

(e) maintaining growth of said pseudocallus cell aggregation in the presence of both said auxin and said cytokinin on said support culture medium to produce pseudocallus cells capable of producing high levels of taxanes;

(f) harvesting the pseudocallus cells; and (g) recovering the taxanes from the harvested pseudocallus cells.

13. The method or claim 12 wherein the explants are obtained from *T. baccata*.

14. The method of claim 12 wherein said growth in steps (d) and (e) occurs in the absence of a taxane production-inhibitory concentration or casein hydrolysate.

15. The method of claim 13, wherein the explants are obtained from *T. baccata* 'resembling Hessei'.

16. The method according to claim 12 wherein at least one of the taxanes is taxol.

17. The method of claim 14, wherein said growth in steps (d) and (e) includes removing $CO_2$ and ethylene from said pseudocallus cells and maintaining a concentration of $CO_2$ in gases in contact with said pseudocallus cells below that normally present in the atmosphere.

18. The method of claim 12, wherein said culturing is carried out until a concentration of taxanes in the pseudocallus cells of at least about 25 μg taxanes/g of the pseudocallus cells, is reached.

19. The method according to claim 12 wherein, said support for the culture medium is a solid or semi-solid and is further selected from the group consisting of a gelling agent, Gelrite®, agar, filter paper, cell mesh, and a micro-porous polypropylene membrane raft, and combinations thereof.

* * * * *